United States Patent
Thorn et al.

(10) Patent No.: US 6,296,669 B1
(45) Date of Patent: Oct. 2, 2001

(54) PROSTHETIC SUSPENSION INSERT

(75) Inventors: Richard P. Thorn; Denise M. Braeger, both of Erie, PA (US)

(73) Assignee: Lord Corporation, Cary, NC (US)

( * ) Notice: Subject to any disclaimer, the term of this patent is extended or adjusted under 35 U.S.C. 154(b) by 0 days.

(21) Appl. No.: 09/341,060

(22) PCT Filed: Dec. 29, 1997

(86) PCT No.: PCT/US97/24208

§ 371 Date: Jun. 28, 1999

§ 102(e) Date: Jun. 28, 1999

(87) PCT Pub. No.: WO98/29059

PCT Pub. Date: Jul. 9, 1998

(51) Int. Cl.[7] ................................................ A61F 2/74
(52) U.S. Cl. .................................................... 623/27
(58) Field of Search ........................... 623/27, 28, 39, 623/40

(56) References Cited

U.S. PATENT DOCUMENTS

| | | | |
|---|---|---|---|
| 3,956,775 | * | 5/1976 | Moore .................................. 3/33 |
| 4,354,397 | * | 10/1982 | Fix ...................................... 74/108 |
| 4,578,082 | * | 3/1986 | Sen-Jung ........................... 623/26 |
| 4,883,493 | * | 11/1989 | Martel et al. ....................... 623/38 |
| 5,133,777 | * | 7/1992 | Arbogast et al. .................. 623/38 |
| 5,458,656 | * | 10/1995 | Phillips ............................... 623/27 |
| 5,800,562 | * | 9/1998 | Wilkinson ........................... 623/27 |
| 5,800,563 | * | 9/1998 | Arbogast et al. .................. 623/25 |
| 5,888,214 | * | 3/1999 | Ochoa ................................ 623/27 |
| 5,961,556 | * | 10/1999 | Thorn ................................. 623/27 |
| 5,984,972 | * | 11/1999 | Huston et al. ..................... 623/35 |
| 6,080,197 | * | 6/2000 | Chen .................................. 623/27 |

* cited by examiner

Primary Examiner—David H. Willse
Assistant Examiner—Alvin Stewart
(74) Attorney, Agent, or Firm—Michael M. Gnibus; Randall S. Wayland

(57) ABSTRACT

A prosthetic insert unit for cushioning shocks in prosthetics is provided. The unit includes attachment member (150 etc.), a lower sleeve (124' etc), a slide bearing (152' etc.) to allow free reciprocal motion therebetween, an elastomeric energy storage member (124' etc.) received in the interior of the sleeve (124' etc.), a piston (134' etc.) cooperative with said elastomer member to compress same, and an anti-rotation mechanism. Preferably, the anti-rotation mechanism is integral with the slide bearing (152' etc.). The elastomer member provides controlled deflection as well as damping for the insert. Preferably, an anti-click element (269 etc.) is provide to minimize rebound clicking. Acoustical elements (268 etc.) may also be included to minimize noise transmission into other areas of the insert.

19 Claims, 3 Drawing Sheets

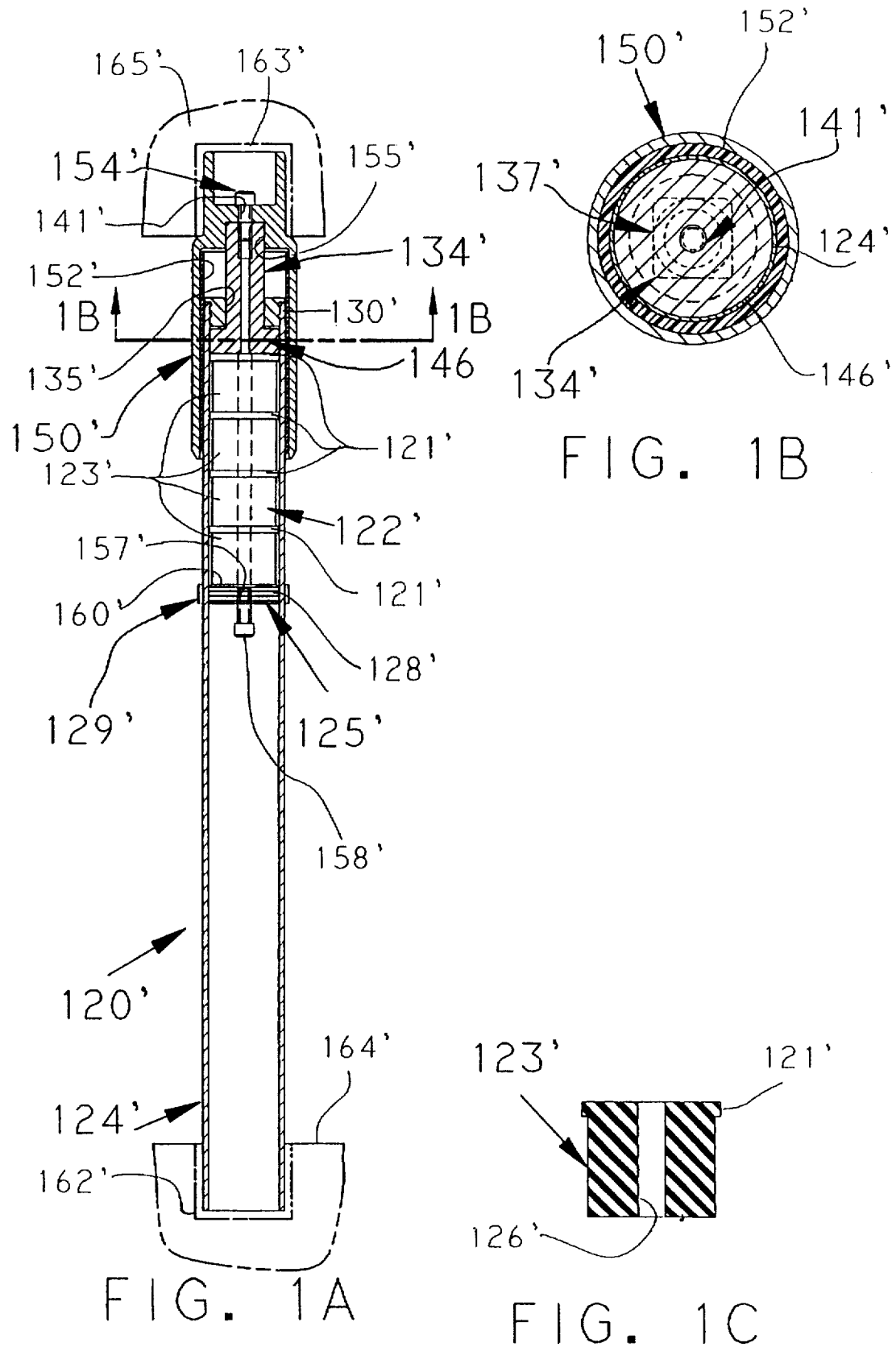

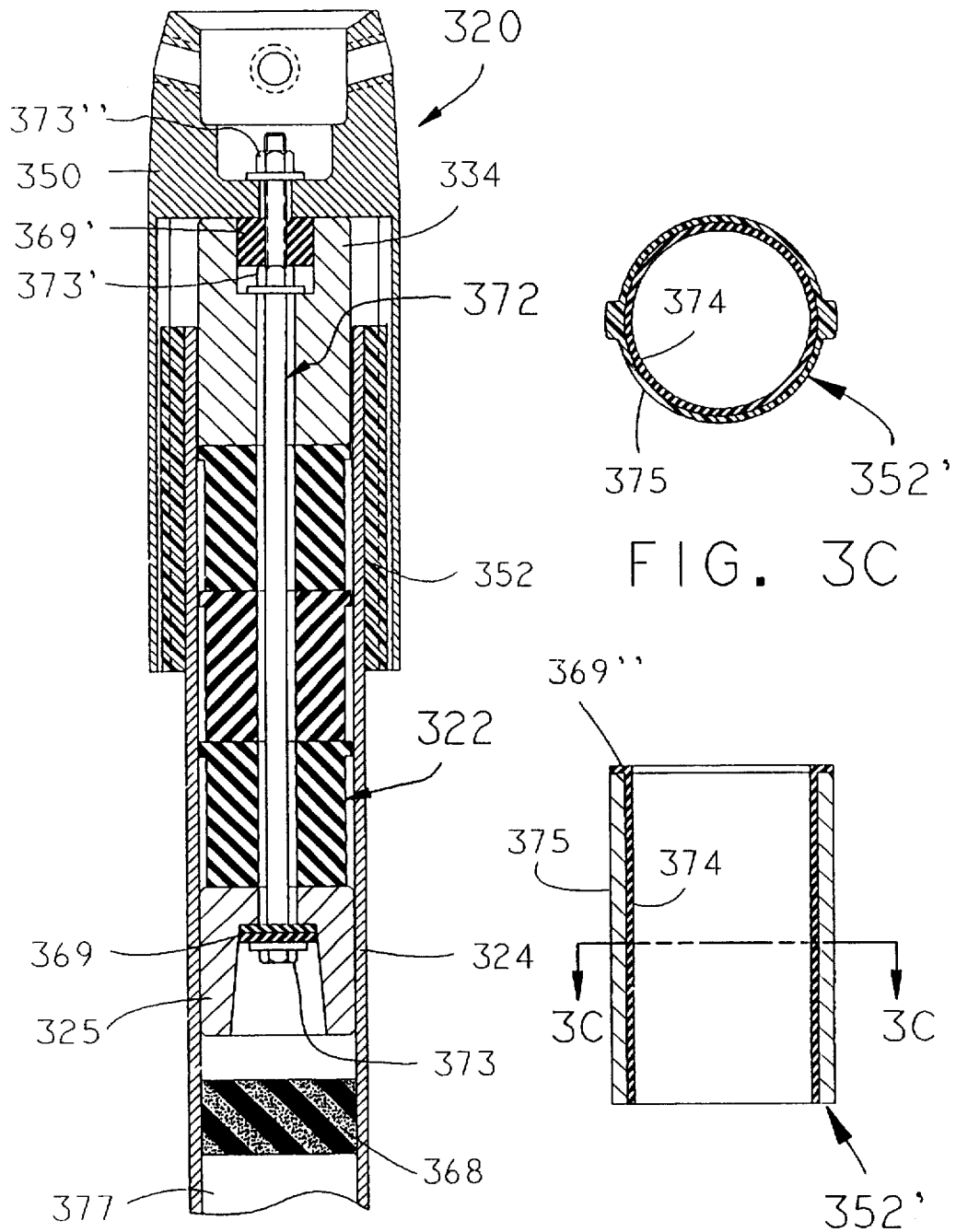

PROSTHETIC SUSPENSION INSERT

BACKGROUND AND SUMMARY OF THE INVENTION

This invention is directed to an insert for prosthetics that is connectable between prosthetic parts. More particularly, the present invention is directed to an elastomer linear energy management unit for inclusion in a prosthetic lower limb or the like.

When a patient moves with a prosthetic limb, such as during walking or athletic activities, the patient's stump and or pelvis experiences shock, and this shock may cause pain and further physical deterioration. This is particularly true in patients with recent amputations. Providing a flexible insert within the patient's prosthetic minimizes such shocks. Examples of prostheses including a flexible element may be found in U.S. Pat. Nos. 4,038,705, 4,883,493, 5,217,500, and 5,458,656, and GB 2 014 855A.

One such flexible elastomeric prosthetic including an elastomeric flexible element is described in DE 196 42 719 A1 to D. Kuczka filed Oct. 17, 1996 entitled "Insert for Prosthetic Devices". Kuczka teaches a prosthetic insert having a prosthetic sleeve (2) and a lower sleeve (10) that at least partially projects into the prosthetic sleeve (2), a bearing (11) to provide low friction movement between the sleeves (2, 10), a counterbearing (9), and a longitudinally displaceable elastomer damping element (8') positioned at the lower end of and within sleeve (2). Threaded disc (5) interconnects to the sleeve (2) and contacts elastomer element (8'). Anti-rotation is provided by element (15) including an external key (16) formed on the sleeve (2) and a slotted bolt (17).

The Kuczka device suffers from a number of problems. First, the anti-rotation feature is external to the sleeve, thus it is bulky and unsightly and provides a large lower profile. Further, the elastomer element is subject to buckling because of its long length. Also, since the elastomer element is positioned near the foot adapter, the large upper tube (2) must extend the distance from the prosthetic part near the knee to the foot adapter, thus providing an unwanted massive and high rotary inertia structure. Moreover, the Kuczka device may click during rebound as stop (13) hits bearing (II). Therefore there is a need for a low inertia, low profile prosthetic insert which solves the problems associated with the prior art. Additionally, in some applications, rotational compliance of the prosthesis is desirable.

The present invention, in one aspect thereof, is directed to prosthetic suspension insert, comprising a lower cylindrical sleeve attachable to a first (lower) prosthetic member; an external attachment member attachable to a second (upper) prosthetic member and surrounding a portion of the cylindrical sleeve; a slide bearing located between an internal peripheral portion of the external attachment member and an external peripheral portion of the cylindrical sleeve, such that the external attachment member may slide freely relative to the cylindrical sleeve; an elastomeric energy storing element positioned within the cylindrical sleeve; a piston cooperative with the external attachment member and slidably positioned within the cylindrical sleeve to engage an axial end portion of the elastomeric energy storage element; and an anti-rotator engaged between the cylindrical sleeve and the external attachment member restraining relative rotation therebetween whereby the elastomeric energy storage element will provide an axial cushioning action to the user during walking.

In another aspect, the elastomeric energy storage member is relatively unstable and collapsible is provided with guide means along its length. The guide means engage the internal surface of the sleeve and provide damping of movement between the sleeve and external attachment means. Preferably, the cylindrical sleeve includes an inner diameter of constant dimension along its length, and the elastomeric energy storing member is positioned entirely within the inner diameter. The elastomeric member may include a plurality of individual units, preferably including a central aperture therethrough, and is preferably precompressed by a desired amount. This precompression may be adjustable.

In yet another aspect which reduces the profile width of the insert, the anti-rotator feature is formed integral with the slide bearing. In this aspect, the slide bearing preferably includes at least one protrusion which slides in at least one groove formed in the external attachment member. In another aspect, the anti-rotator includes a compliant member to provide limited rotation between the sleeve and the attachment member. Preferably, the compliant member is a annular elastomer member bonded to the cylindrical sleeve and integral with the slide bearing.

In another aspect, the insert includes an anti-click element, such as one or more elastomeric washers, to minimize rebound clicking during use. Optionally, or additionally, internal noise transmission may be further retarded by use of an acoustical treatment, such as a open cell foam contained in the insert, to deaden sounds generated by action of the insert. Other features, advantages and characteristics of the present invention will become apparent after a reading of the following detailed description of the preferred embodiments.

BRIEF DESCRIPTION OF THE DRAWINGS

The following figures depict the preferred embodiments of the present invention, like items bearing like reference numerals and, in which FIG. 1A is a cross-sectional side view of an embodiment of the prosthetic suspension insert in accordance with the present invention;

FIG. 1B is an end view of the piston used in the FIG. 1A embodiment;

FIG. 1C is a cross sectioned side view of an elastomer element used in the FIG. 1A embodiment;

FIG. 3A is a cross sectioned side view of another alternate insert embodiment in accordance with the present invention;

FIG. 3B is a cross sectioned side view of an alternate slide bearing including a complaint member; and FIG. 3C is a cross sectioned side view of the slide bearing of FIG. 3B.

DETAILED DESCRIPTION OF THE PREFERRED EMBODIMENTS

Figures 2A, 2B:
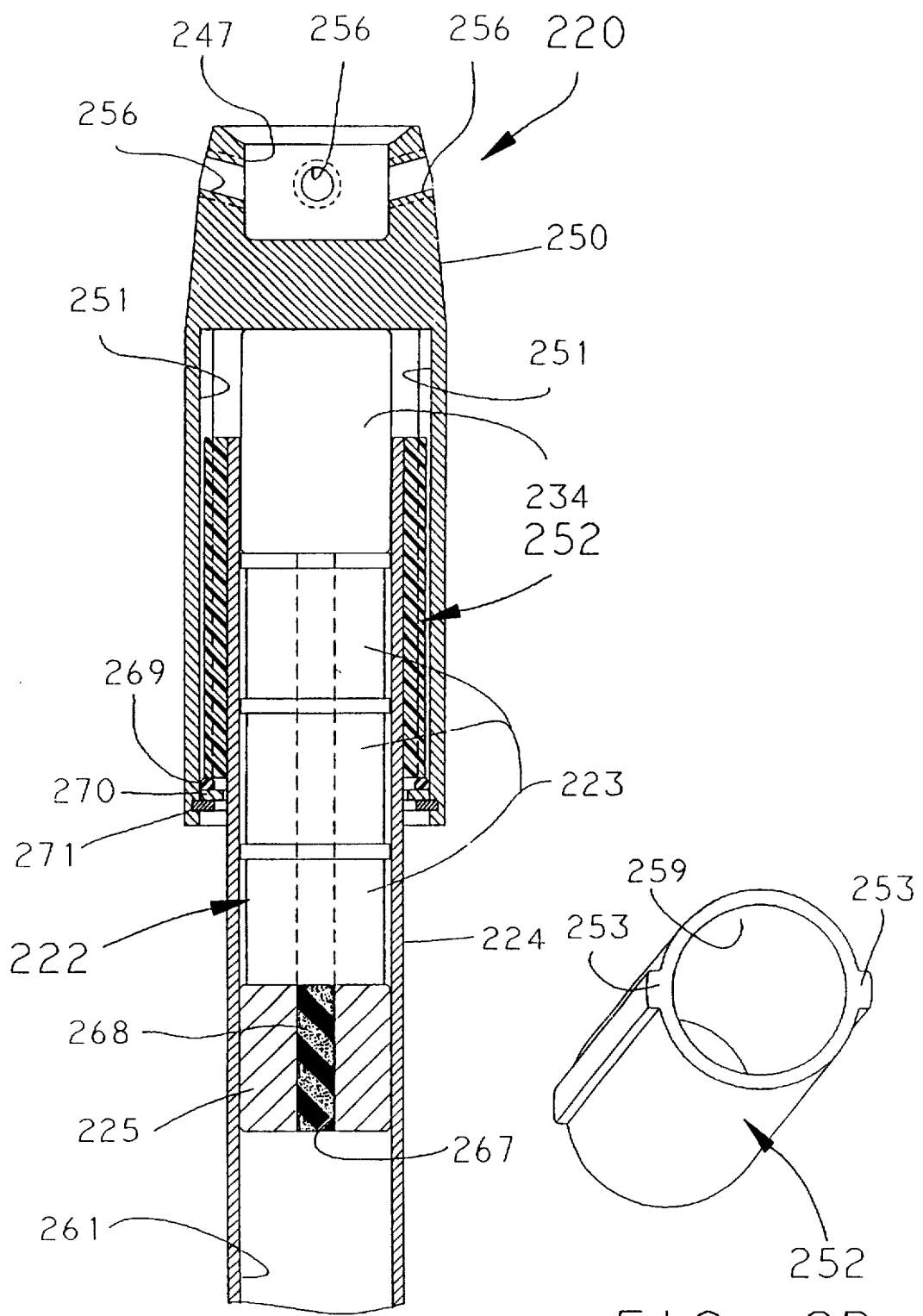
FIG. 2A is a cross sectioned side view of an alternate insert embodiment in accordance with the present invention.
FIG. 2B is a perspective view of the slide bearing used in FIG. 2A.

As best seen in FIG. 1A, the insert 120' in accordance with the present invention provides resiliency which effectively mimics that provided by the human leg, such that gait symmetry is effectively achieved. In use, the insert 120' will be received in an adapter 162' in a prosthetic foot 164' or the like and is also received in an adapter 163', for example, in a stump cap 165' or the like. Upper and lower ends of unit 120' are received in, for example, 31 mm adapters manufactured by Hosmer US identified by part No. 39504 or 30 mm adapters manufactured by Otto Bock identified as part no. 2R38 or 4R52. However, it will be understood that the specified adapter is regarded as merely exemplary and that the unit 120' of the present invention could be configured to operate with other adapters, as well. Notably, the need for an upper adapter will be eliminated in the later embodiments. Moreover, it should be understood that the insert in accordance with the present invention finds applicability in lower leg prosthetics. However, the insert may also be applied to prosthetics for above-the-knee amputees where a mechanical knee joint is implemented.

A lower aluminum cylindrical sleeve 124' extends a major portion of a distance between the prosthetic foot 164' and the cap 165'. The sleeve 124' is stopped by an internal plug 125'. The sleeve 124' is crimped at 128' to secure the plug 125' in the desired position. Sleeve 124' is provided with an external reinforcement ring 129' in those applications where sleeve 124' is a structural member. In this embodiment, the elastomeric energy storage means, i.e., the elastomer member 122' is made up of a plurality of generally cylindrical units 123' as shown in FIG. 1C. Each cylindrical unit 123' has a radially extending flange 121' and a aperture 126' therethrough. The addition of bore 126' through each elastomer element 123' provides the desired spring rate by allowing the appropriate bulge characteristics for the leg prosthesis application. The plurality of flanges 121' fit snugly in sleeve 124' and serving as guide means to prevent buckling of the elastomer column. This elastomeric member 122' is inherently unstable because of its high length L to diameter D ratio. Generally, it is known to persons of skill in the art that L/D ratios of greater than two tend to be unstable.

The close fitting sleeve 124' engages flanges 121' and provides means to stabilize the collapse of the elastomer when engaged by the piston 134' during compression. The collapse of elastomeric member 122' into contact with the inner surface of sleeve 124' will produce damping to restrain relative motion between the sleeve 124' and elastomer means 122'. The elastomeric means 122' is preferably made of natural rubber, although other materials such as urethane and Hytrel plastics may be used, as well. The durometer of the material in the elastomeric means 122' preferably falls in the range of between 50 and 80 Shore A. Preferably, the radially outermost surface of guide means 121' will be provided with a lubricant, such as a Teflon-filled grease, to reduce wear. Alternatively, other suitable lubricating mechanisms may be provided.

The opposite (upper) end of sleeve 124' is closed by a cylindrical collar 130' which slidingly receives piston rod 134'. The piston head 146' on piston 134' engages the upper axial end of elastomeric means 122'. The majority of the length of piston rod 134' has a square configuration (FIG. 1B) which is received in a like shaped opening 135' in cylindrical collar 130' to prevent relative rotation. This provides a compact anti-rotation (anti-rotator) feature.

A external attachment member 150' which includes a lower generally cylindrical sleeve portion is received over the upper end of sleeve 124'. A slide bearing 152' of low friction material is received by and adhered to the internal periphery of attachment means 150' to facilitate axial movement of attachment member 150' relative to sleeve 124'. An axial bore 141' formed through piston 134' is threaded and receives a fastener 154'. This fastener 154' secures attachment member 150' to piston rod 134'. Likewise, a cylindrical portion 137' of piston rod 134' is received in a similarly-shaped recess 155' in attachment member 150'. Piston 134' will move concurrently with external attachment member 150' to collapse elastomeric means 122'. The square shaft in square opening 135' prevents relative rotation between sleeve 124' and attachment member 150'.

For appropriate applications, plug 125' can have a bore 157' that is threaded to receive an adjustment bolt 158'. Bolt 158' bears against washer 160' and by adjusting its position relative to plug 125', the amount of precompression of elastomeric member 122' can be varied. The amount of preload provided can be adjusted by controlling the length of elastomeric means 122'. It will typically be desired to provide a preload equal to between 10% and 20% of the normal load applied to the elastomeric means 122'. The ultimate load will compress the elastomer up to 40% of its uncollapsed length.

FIG. 2A illustrates another embodiment of the insert 220 including an aluminum external attachment member 250 having an integral adapter for securing to the prosthetic stump or cap (not shown) or the like, and an aluminum lower sleeve 224 which secures to a prosthetic foot, adapter, or the like (not shown). For clarity, a large portion of the lower sleeve 224 which extends the majority of the distance between the prosthetic foot and stump cap is not shown. The stump or cap member may be attached to the attachment member 250 by inserting a square-shaped post (ex. a Hosmer 29406) thereon into square-shaped pocket 247 and securing thereto via threaded set screws (not shown) received in threaded holes 256. An elastomer energy storage element 222 is received within the inner dimension (diameter) of the sleeve 224. Preferably elastomer element 222 comprises a plurality of individual elements 223 as is shown in FIG. 1C.

In this embodiment, the anti-rotation mechanism (anti-rotator) is integrated into the slide bearing 252. The external attachment member 250 includes at least one, and preferably a plurality of grooves 251 formed along its length for receiving at least one, and preferably a plurality of protrusions 253 formed on the periphery of the Nylatron slide bearing 252 (FIG. 2B). Preferably two radially opposed protrusions 253 are provided. The internal diametral surface 259 of slide bearing 252 is bonded to the outer diameter of sleeve 224 with suitable adhesive, such as an epoxy or cyanoacrylate. The protrusions 253 cooperate with the grooves 251 to restrain rotation, but allow relative axial displacements.

A nylon stop plug 225 is adhesively bonded via an epoxy or a cyanoacrylate adhesive to the inside surface 261 of the lower sleeve 224. The stop plug 225 includes a hole 267 therethrough which includes a open cell foam plug 268 therein. The foam plug 268 functions as an acoustical barrier to prevent noise made via compression of the elastomer member 222 from transmitted to other portions of the insert, and in particular from resonating inside the lower chamber-like portion of sleeve 224. Optionally, the acoustical barrier may be placed inside the lower end of sleeve 224 itself. The puck-shaped nylon piston 234 cooperates and moves in conjunction with the attachment member 250 and is slidably received in close fit relation to the inner dimension 261 of sleeve 224. The piston 234 engages an axial end of the elastomer member 222 to compress same in use. The lower assembly comprising sleeve 224 with slide bearing 252 and plug 225 adhered thereto is assembled with the elastomer member 222 and piston 234 and inserted into the attachment member 250.

An anti-click elastomer washer 269 or o-ring is inserted adjacent to the lower end of the slide bearing 252. A rigid steel seat washer 270 is then inserted over elastomer washer 269 and the assembly 220 is precompressed in the axial direction, such that a retaining c-clip 271 may be installed. The c-clip 271 holds the insert assembly 220 together. The position of the clip 271 and thickness of the washer 270 (such as by adding additional washers) may be adjusted to vary the precompression on the elastomer member 222. Alternatively, spacers (not shown) may be added at the interface of the piston 234 and elastomer member or at the lower end of the elastomer member 222. During walking, the washer 269 eliminates clicking as the elastomer element 222 rebounds after the compression stroke. It should be noted that the slide bearing 252 pulls away from the seat washer 270 during compression. It should also he recognized that by having the elastomer element 222 installed entirely within the confines of the sleeve 224, the diameter of the lower sleeve 224 can be made smaller, thereby providing lower profile. Moreover, the highest mass portion of the insert is located close to the knee, thus, advantageously providing a low rotary inertia. Further, the anti-rotation feature is preferably made integral to the slide bearing providing a streamlined appearance.

FIG. 3A illustrates another embodiment of the prosthetic suspension insert 320 in accordance with the present invention which includes a central fastener assembly 372 for providing precompression to the elastomer energy storage element 322. Compliant elastomer washers 369 are provided at the lower end of fastener assembly 372 to prevent rebound clicking. Likewise, a compliant annular puck 369' is preferably provided at the top of assembly 372 to prevent rattling of the fastener assembly 372 within the attachment member 350 when under enough load to alleviate the precompression. Fasteners 373, 373' are turned to adjust the amount of precompression, whilst fastener 373" secures the assembly to the attachment member 250. Nylon piston 334 is slidably received in the lower sleeve 324 as in the previous embodiments. Similarly, the Nylatron slide bearing 352, the same as shown in FIG. 2B, is bonded to the outer peripheral surface of the sleeve 324 and the plug 325 is bonded to the internal surface of the sleeve 324. A plug of open cell foam 368 is provided as an acoustical barrier to prevent transmission of noise into the lower cavity 377 of sleeve 324 which could function as a resonant chamber.

FIG. 3B and 3C illustrate an alternate embodiment of the slide bearing 352' which may be interchanged with the slide bearing of FIG. 2A or 3A. This slide bearing 352' includes rotational compliance provided by a thin elastomer layer 374 which is bonded to the outer Nylatron bearing portion 375. The elastomer layer 374 is then preferably hot PV bonded to the outer diameter of the sleeve 324. By way of example, and not to be considered limiting, the elastomer layer 374 is comprised of a 0.04 inch (1 mm) thick annulus and manufactured from natural rubber of a hardness of between 44 and 52 Shore A durometer. However, any other suitable elastomer or bonding method may be used. The elastomer layer 374 may include a washer-like portion 369'" formed at the lower end of the bearing portion 375 to provide the anti-click feature, if needed, such as for example, when installed in the FIG. 2A embodiment. This slide bearing 352' provides a rotational compliance to the suspension insert. For example, under normal expected operating loads, about +/−5° of torsional motion is accommodated within the insert.

Various changes, alternatives and modifications will become apparent to one of ordinary skill in the art following a reading of the foregoing specification. It is intended that all such changes, alternatives and modifications as fall within the scope of the appended claims be considered part of the present invention.

What is claimed is:

1. A prosthesis insert, characterized by:
   a) a lower cylindrical sleeve attachable to a first prosthetic member;
   b) an external attachment member attachable to a second prosthetic member and surrounding a portion of said cylindrical sleeve;
   c) a slide bearing located between said external attachment member and said cylindrical sleeve such that said attachment member may slide freely relative to said cylindrical sleeve;
   d) an elastomeric energy storing element positioned within said cylindrical sleeve, said elastomeric storage device including a central aperture therethrough;
   e) a piston cooperative with said external attachment member and positioned within an upper end of said cylindrical sleeve to operatively engage an axial end portion of said elastomeric energy storing element; and
   f) an anti-rotation mechanism engaged between said cylindrical sleeve and said external attachment member to restrain relative rotation therebetween.
   whereby said elastomeric energy storage element will provide a cushioning action to a user during walking.

2. A prosthesis suspension insert of claim 1 further characterized in that said elastomeric energy storing element is relatively unstable and collapsible in that its length is substantially longer than its width.

3. A prosthesis suspension insert of claim 2 further characterized in that said elastomeric energy storing element includes guides positioned along its length.

4. A prosthesis suspension insert of claim 1 further characterized in that said cylindrical sleeve includes an inner diameter of constant dimension along its length, and said elastomeric energy storing means is positioned entirely within said inner diameter.

5. A prosthesis suspension insert of claim 1 further characterized in that said elastomeric energy storing element further comprises a plurality of individual units.

6. A prosthesis suspension insert of claim 1 further characterized by providing precompression to said elastomeric energy storing element.

7. A prosthesis suspension insert of claim 6 further characterized in that said precompression can be adjusted by varying an amount of preload on said elastomeric energy storing element.

8. A prosthesis suspension insert of claim 7 further characterized by a fastener assembly extending through said elastomeric energy storing element.

9. A prosthesis suspension insert of claim 1 further characterized in that said anti-rotation mechanism is integral with said slide bearing.

10. A prosthesis suspension insert of claim 9 further characterized in that said slide bearing includes at least one protrusion which slides in at least one groove formed in said attachment member.

11. A prosthesis suspension insert of claim 1 further characterized in that a compliant member to provide limited rotation is provided.

12. A prosthesis suspension insert of claim 11 further characterized in that said compliant member is integral with said slide bearing.

13. A prosthesis suspension insert of claim 12 further characterized in that said compliant member includes a annular elastomer member bonded to said cylindrical sleeve.

14. A prosthesis suspension insert of claim 1 further characterized in that said anti-rotation mechanism comprises a square shaft portion on a shaft of said piston and a square opening in a guide disk associated with an end of said sleeve whereby said square shaft portion can slide freely in said square opening.

15. A prosthesis suspension insert of claim 1 further characterized by an anti-click element to minimize rebound clicking.

16. A prosthesis suspension insert of claim 15 further characterized in that said anti-click element includes an elastomer washer.

17. A prosthesis suspension insert of claim 1 further characterized by an acoustical treatment to prevent transmission of noise generated by action of said insert.

18. A prosthesis suspension insert of claim 1 further characterized by a lubricated surface on a portion of said elastomeric energy storing element contacting said sleeve.

19. A prosthesis characterized in that an insert in accordance with one or more of claims 1–18 is provided.

* * * * *